US00PP20032P2

(12) United States Plant Patent
Iwaki et al.

(10) Patent No.: US PP20,032 P2
(45) Date of Patent: May 26, 2009

(54) ***PETUNIA* PLANT NAMED 'SUNSURFPINKAI'**

(50) Latin Name: *Petunia×hybrida*
Varietal Denomination: Sunsurfpinkai

(75) Inventors: Kazunari Iwaki, Kanagawa (JP); Takeshi Kanaya, Shiga (JP); Yasuko Isobe, Shiga (JP)

(73) Assignee: Suntory Flowers Limited, Tokyo (JP)

( * ) Notice: Subject to any disclaimer, the term of this patent is extended or adjusted under 35 U.S.C. 154(b) by 41 days.

(21) Appl. No.: 12/077,209

(22) Filed: Mar. 17, 2008

(51) Int. Cl.
*A01H 5/00* (2006.01)

(52) U.S. Cl. ..... Plt./356
(58) Field of Classification Search ..... Plt./356
See application file for complete search history.

*Primary Examiner*—Annette H Para
(74) *Attorney, Agent, or Firm*—C. A. Whealy

(57) ABSTRACT

A new and distinct cultivar of *Petunia* plant named 'Sunsurfpinkai', characterized by its trailing plant habit; vigorous growth habit; freely branching and flowering plant habit; long flowering period; medium-sized light pink to pinkish white-colored flowers; and good garden performance.

1 Drawing Sheet

Botanical designation: *Petunia×hybrida*.
Cultivar denomination: 'SUNSURFPINKAI'.

BACKGROUND OF THE INVENTION

The present invention relates to a new and distinct cultivar of *Petunia,* botanically known as *Petunia×hybrida* and hereinafter referred to by the name 'Sunsurfpinkai'.

The new *Petunia* is a product of a planned breeding program conducted by the Inventors in Higashiomi, Shiga, Japan. The objective of the breeding program is to create new *Petunia* cultivars with attractive foliage and flower coloration.

The new *Petunia* originated from a cross-pollination made by the Inventors in August, 2003 in Higashiomi, Shiga, Japan of the *Petunia×hybrida* cultivar Madness Rose Star, not patented, as the female, or seed, parent with a proprietary selection of *Petunia×hybrida* identified as code number P55h5, not patented, as the male, or pollen, parent. The new *Petunia* was discovered and selected by the Inventors as a single flowering plant within the progeny of the stated cross-pollination in a controlled environment in Higashiomi, Shiga, Japan.

Asexual reproduction of the new *Petunia* by terminal cuttings in a controlled environment in Higashiomi, Shiga, Japan since September, 2005, has shown that the unique features of this new *Petunia* are stable and reproduced true to type in successive generations.

SUMMARY OF THE INVENTION

The cultivar Sunsurfpinkai has not been observed under all possible environmental conditions. The phenotype may vary somewhat with variations in environment and cultural practices such as temperature, daylength and light intensity without, however, any variance in genotype.

The following traits have been repeatedly observed and are determined to be the unique characteristics of 'Sunsurfpinkai'. These characteristics in combination distinguish 'Sunsurfpinkai' as a new and distinct cultivar of *Petunia*:

1. Trailing plant habit.
2. Vigorous growth habit.
3. Freely branching and flowering plant habit.
4. Long flowering period.
5. Medium-sized light pink to pinkish white-colored flowers.
6. Good garden performance.

Plants of the new *Petunia* can be compared to plants of the female parent, the cultivar Madness Rose Star. Plants of the new *Petunia* differ from plants of the cultivar Madness Rose Star in the following characteristics:

1. Plants of the new *Petunia* are more trailing than and not as upright as plants of the cultivar Madness Rose Star.
2. Plants of the new *Petunia* and the cultivar Madness Rose Star differ in flower color as plants of the cultivar Madness Rose Star have pink-colored flowers with a central white-colored star pattern.

Plants of the new *Petunia* can be compared to plants of the male parent selection. Plants of the new *Petunia* differ from plants of the male parent selection in the following characteristics:

1. Plants of the new *Petunia* have larger flowers than plants of the male parent selection.
2. Plants of the new *Petunia* and the male parent selection differ in flower color as plants of the male parent selection have white-colored flowers.

Plants of the new *Petunia* can also be compared to plants of the cultivar Sunsurfmicshipho, disclosed in U.S. Plant Pat. No. 18,594. In side-by-side comparisons conducted in Higashiomi, Shiga, Japan, plants of the new *Petunia* and the cultivar Sunsurfmicshipho differed in the following characteristics:

1. Plants of the new *Petunia* were more trailing than plants of the cultivar Sunsurfmicshipho.
2. Plants of the new *Petunia* were smaller than plants of the cultivar Sunsurfmicshipho.
3. Plants of the new *Petunia* had larger flowers than plants of the cultivar Sunsurfmicshipho.

4. Plants of the new *Petunia* and the cultivar Sunsurfmicshipho differed slightly in flower color.

BRIEF DESCRIPTION OF THE PHOTOGRAPHS

The accompanying colored photographs illustrate the overall appearance of the new *Petunia,* showing the colors as true as it is reasonably possible to obtain in colored reproductions of this type. Colors in the photographs may differ slightly from the color values cited in the detailed botanical description which accurately describe the colors of the new *Petunia*.

The photograph at the top of the sheet comprises a top perspective view of a typical flowering plant of 'Sunsurfpinkai' grown in a container.

The photograph at the bottom of the sheet is a close-up view of typical flowers of 'Sunsurfpinkai'.

DETAILED BOTANICAL DESCRIPTION

The aforementioned photographs and following observations, measurements and values describe plants grown in Higashiomi, Shiga, Japan, under commercial practice during the spring in an outdoor nursery day temperatures averaging 22° C. and night temperatures averaging 12° C. Plants had been growing for about four months when the photographs and description were taken. In the following description, color references are made to The Royal Horticultural Society Colour Chart, 2001 Edition, except where general terms of ordinary dictionary significance are used.

Botanical classification: *Petunia×hybrida cultivar* Sunsurfpinkai.

Parentage:

*Female, or seed, parent.*—*Petunia×hybrida* cultivar Madness Rose Star, not patented.

*Male, or pollen, parent.*—Proprietary selection of *Petunia×hybrida* identified as code number P55h5, not patented.

Propagation:

*Type.*—By terminal cuttings.

*Time to initiate roots.*—About one week at temperatures of 20° C. to 25° C.

*Time to produce a rooted young plant.*—About three weeks at temperatures of 20° C. to 25° C.

*Root description.*—Fine, fibrous, fleshy; light brown in color.

*Rooting habit.*—Freely branching.

Plant description:

*Plant and growth habit.*—Trailing plant habit. Freely branching habit with about 15 lateral branches developing per plant; pinching enhances lateral branch development. Vigorous growth habit.

*Plant height.*—About 12.5 cm.

*Plant diameter.*—About 29.5 cm.

Lateral branch description:

*Length.*—About 17 cm.

*Diameter.*—About 2.5 mm.

*Internode length.*—About 1 cm.

*Strength.*—Strong, flexible.

*Aspect.*—Decumbent.

*Texture.*—Pubescent.

*Color.*—Close to 137C.

Foliage description:

*Arrangement.*—Before flowering, alternate, simple; after flowering, opposite, simple.

*Length.*—About 2.6 cm.

*Width.*—About 2 cm.

*Shape.*—Elliptic.

*Apex.*—Broadly acute.

*Base.*—Obtuse.

*Margin.*—Entire.

*Texture, upper and lower surfaces.*—Pubescent.

*Venation pattern.*—Pinnate; reticulate.

*Color.*—Developing and fully expanded foliage, upper surface: Close to 137C; venation, close to 145B. Developing and fully expanded foliage, lower surface: Close to 146B; venation, close to 145B.

*Petiole.*—Length: About 4.4 mm. Diameter: About 2.2 mm. Texture, upper and lower surfaces: Sparsely pubescent. Color, upper and lower surfaces: Close to 145B.

Flower description:

*Flower arrangement and habit.*—Single salverform flowers arising from leaf axils. Freely flowering habit with usually about 18 open flowers per plant. Flowers face upright or outwardly. Flowers not fragrant.

*Natural flowering season.*—Plants of the new *Petunia* initiate and develop flowers about three to four weeks after planting. Long flowering period; flowering commences naturally during the spring and plants flower continuously throughout the summer until late autumn in Japan. Flowers not persistent.

*Flower longevity.*—Individual flowers last about seven to ten days on the plant.

*Flower diameter.*—About 5.1 cm.

*Flower length (depth).*—About 4.6 cm.

*Throat diameter.*—About 1 cm.

*Tube diameter, base.*—About 2.7 mm.

*Tube length.*—About 2.4 cm.

*Flower bud.*—Shape: Cylindrical. Length: About 3.5 cm. Diameter: About 7.5 mm. Color: Close to 144C; towards the apex, close to 84C.

*Corolla.*—Arrangement: Five petals fused at the base and opening into a flared trumpet. Petal length from throat: About 2.3 cm. Petal width: About 2.2 cm. Petal shape: Spatulate. Petal apex: Cuspidate. Petal margin: Entire; slightly undulate. Petal texture, upper and lower surfaces: Smooth, glabrous; velvety. Throat texture: Smooth, glabrous. Tube texture: Sparsely pubescent. Color: Petal, when opening, upper surface: Close to 75B. Petal, when opening, lower surface: Close to 76C. Petal, fully opened, upper surface: Close to 76C; venation, close to 72A; color becoming closer to 69D with development. Petal, fully opened, lower surface: Close to 76D; venation, close to N144A. Throat: Close to 155B; venation, close to 152B. Tube: Close to 155B; venation, close to N144A.

*Calyx.*—Arrangement: One star-shaped calyx tube with five sepals fused at the base per flower. Sepal length: About 9 mm. Sepal width: About 2.9 mm. Sepal shape: Narrowly elliptic. Sepal apex: Obtuse. Sepal margin: Entire. Sepal texture, upper and lower surfaces: Pubescent. Color, upper and lower surfaces: Close to 143B.

*Peduncles.*—Length: About 1.2 cm. Diameter: About 1.6 mm. Strength: Strong. Texture: Sparsely pubescent. Color: Close to 137C.

*Reproductive organs.*—Stamens: Quantity/arrangement: Five per flower. Stamen length: About 1.6 cm to 1.8 cm. Anther shape: Ellipsoidal. Anther size: About 1.9 mm by 2.5 mm. Anther color: Close to 155D. Pollen amount: Moderate. Pollen color: Close to 155D. Pistils: Quantity: One per flower. Pistil length: About 1.7 cm. Style color: Close to 144C. Stigma shape: Transversely ellipsoidal. Stigma color: Close to 144B. Ovary color: Close to 143C.

*Seed/fruit.*—Seed and fruit development have not been observed on plants of the new *Petunia*.

Garden performance: Plants of the new *Petunia* have been observed to have good garden performance and to tolerate rain, wind and temperatures ranging from about 5° C. to about 35° C.

Pathogen/pest resistance: Plants of the new *Petunia* have not been observed to be resistant to pests and pathogens common to *Petunia*.

It is claimed:

1. A new and distinct *Petunia* plant named 'Sunsurfpinkai' as illustrated and described.

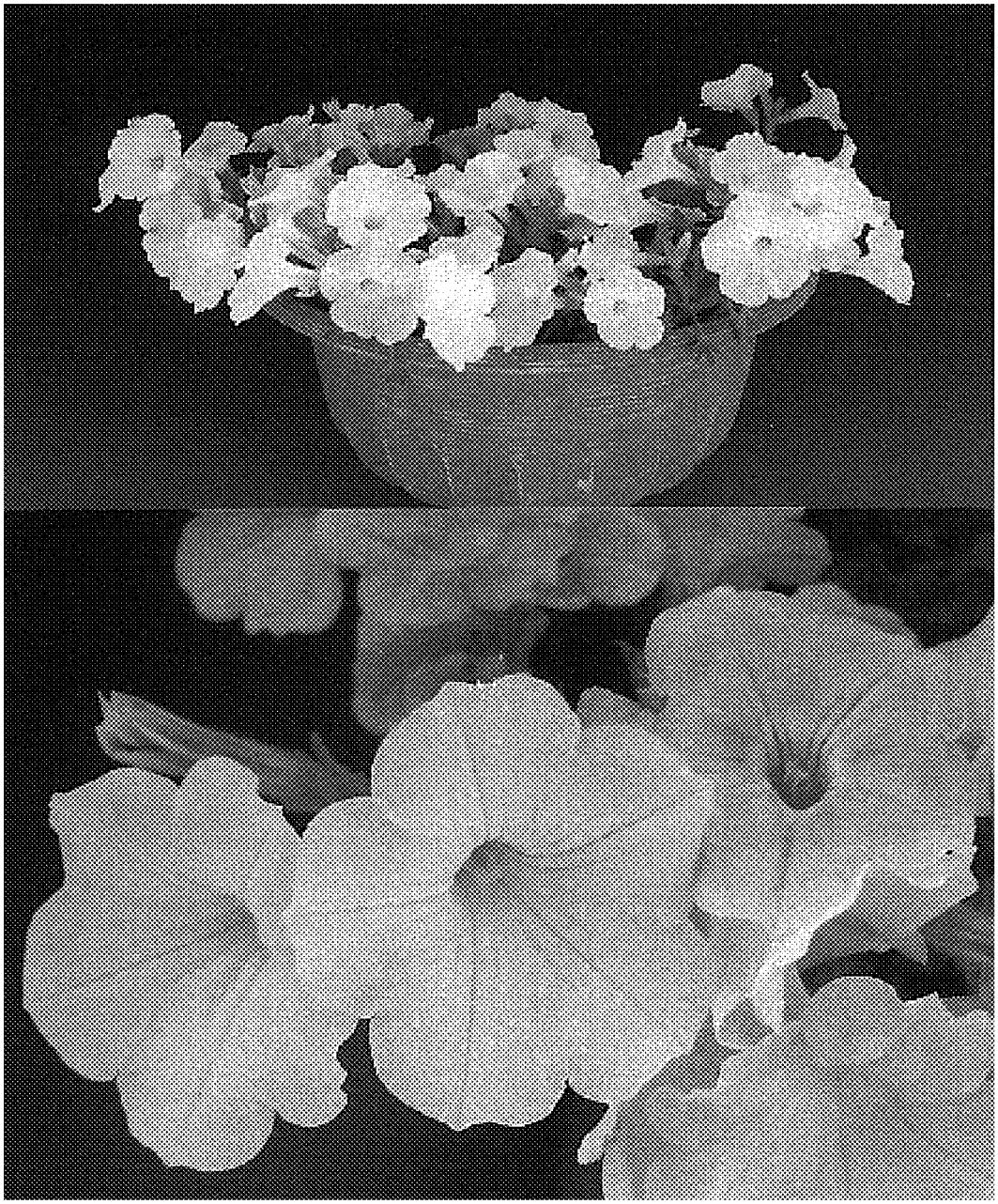

* * * * *